(12) United States Patent
Pan et al.

(10) Patent No.: US 11,733,145 B2
(45) Date of Patent: Aug. 22, 2023

(54) HIGH-PRESSURE HELIUM SHALE POROSITY TESTING DEVICE AND METHOD

(71) Applicant: Northeast Petroleum University, Daqing (CN)

(72) Inventors: Zhejun Pan, Daqing (CN); Tong Wu, Daqing (CN)

(73) Assignee: Northeast Petroleum University, Daqing (CN)

( * ) Notice: Subject to any disclaimer, the term of this patent is extended or adjusted under 35 U.S.C. 154(b) by 55 days.

(21) Appl. No.: 17/582,157

(22) Filed: Jan. 24, 2022

(65) Prior Publication Data

US 2023/0152200 A1 May 18, 2023

(30) Foreign Application Priority Data

Nov. 15, 2021 (CN) .......................... 202111344836.X

(51) Int. Cl.
*G01N 15/08* (2006.01)
*G01N 33/24* (2006.01)

(52) U.S. Cl.
CPC ..... *G01N 15/0826* (2013.01); *G01N 15/0806* (2013.01); *G01N 33/24* (2013.01)

(58) Field of Classification Search
CPC .... G01N 15/00; G01N 15/08; G01N 15/0806; G01N 15/0826; G01N 33/24
See application file for complete search history.

(56) References Cited

U.S. PATENT DOCUMENTS 7,131,317 B2 * 11/2006 Lenormand ........ G01N 15/0826
73/38

FOREIGN PATENT DOCUMENTS

| CN | 111272636 A | * | 6/2020 | ............. G01N 15/08 |
| CN | 212483266 U | * | 2/2021 | ............. G01N 15/08 |

* cited by examiner

*Primary Examiner* — Nguyen Q. Ha
(74) *Attorney, Agent, or Firm* — Greenberg Traurig, LLP

(57) ABSTRACT

The present disclosure provides a high-pressure helium shale porosity testing device and method. The device comprises a reference cylinder, a pressure cylinder, a sample cylinder, a differential pressure sensor, a pressure gauge, an venting and vacuumizing system, a temperature control system and a tubing and valve system, wherein the reference cylinder is respectively connected with a helium source, the pressure cylinder and the sample cylinder through the tubing and valve system, the differential pressure sensor is configured to measure changes of pressure difference between the sample cylinder and the pressure cylinder, the pressure gauge is configured to measure pressure at the pressure cylinder, the sample cylinder is further connected with the venting and vacuumizing system through the tubing and valve system, and the temperature control system is used for controlling the temperature of the whole device.

5 Claims, 3 Drawing Sheets

HIGH-PRESSURE HELIUM SHALE POROSITY TESTING DEVICE AND METHOD

CROSS REFERENCE TO RELATED APPLICATION(S)

This patent application claims the benefit and priority of Chinese Patent Application No. 202111344836.X, filed on Nov. 15, 2021, the disclosure of which is incorporated by reference herein in its entirety as part of the present application.

TECHNICAL FIELD

The present disclosure relates to the technical fields of petroleum exploration and development, in particular to a high-pressure helium shale porosity testing device and method.

BACKGROUND ART

The shale oil is regarded as an important petroleum replacement resource in China, and development of the shale oil is of important strategic and practical significance. The shale oil is a petroleum resource existing in a shale formation system, including the oil in shale, tight carbonate and clastic rocks, and the main part of the shale oil exists in matrix pores of the shale and those tight rocks. Therefore, the porosity of the shale is of great significance to the calculation of shale oil and gas resource quantity and the yield of shale oil and gas. The helium porosity is mainly obtained by firstly testing the true density of shale and then calculating according to the relation between the porosity and the true and apparent densities.

At present, a low-pressure helium method is mainly adopted for testing the porosity of shale. Using low-pressure helium has the advantages that the equipment is simple, the cost is low and the low-pressure helium is regarded as ideal gas, so that the calculation method is simple, and the error of using low-pressure sensor in the measured pressure range is small. In addition, much of currently used similar equipment is operating at room temperature, however, porosity under formation temperature and pressure conditions is more of practical significance, and it is also necessary to measure porosity at different pressures since changes in porosity are also caused by changes in pressure during production.

According to the existing low-pressure helium porosity measurement principle, a reference cylinder with a known volume is used and connected with a sample cylinder through tubing and a valve. The reference cylinder is filled with helium at two atmospheric pressures before an experiment starts, then the valve is opened to enable the helium to flow into the sample cylinder from the reference cylinder, and the true density and the porosity of a sample are calculated through pressure change. If the same design is used, and only the pressure range that can be borne by the device is increased, a pressure sensor with a larger measuring range needs to be used. However, the error of the pressure sensor is generally 0.1% of the full range of the pressure sensor, so that the error of pressure difference results obtained before and after the experiment under high pressure is large, nevertheless, the pressure difference is the most important parameter for calculating the porosity. If the pressure sensor with higher precision is used, the cost is too high, and the improvement degree of the test result is limited. In addition, helium is away from the ideal gas state at high pressure, a computational model of real gas is required to be used, and therefore, the design scheme and experimental method of the device are required to be updated when the porosity of shale is measured by using high pressure helium.

SUMMARY

The present disclosure aims to provide a high-pressure helium shale porosity testing device and method so as to solve the problems in the prior art and can realize high-precision porosity testing under the conditions of simulating formation temperature and pressure under the high-pressure helium condition. Meanwhile, the relation between the diffusing amount of high-pressure helium in shale and the time can be obtained.

In order to achieve the purpose, the present disclosure provides the following scheme:

The present disclosure provides a high-pressure helium shale porosity testing device, comprising a reference cylinder, a pressure cylinder, a sample cylinder, a differential pressure sensor, a pressure gauge, a venting and vacuumizing system, a temperature control system and a tubing and valve system, wherein the reference cylinder is respectively connected with a helium source, the pressure cylinder and the sample cylinder through the tubing and valve system, the differential pressure sensor is configured to measure changes of pressure difference between the sample cylinder and the pressure cylinder, the pressure gauge is configured to measure pressure at the pressure cylinder, the sample cylinder is further connected with the venting and vacuumizing system through the tubing and valve system, and the temperature control system is used for controlling the temperature of the whole device.

Preferably, the tubing and valve system comprises tubings and valves, a first valve is arranged on the tubing between the helium source and the reference cylinder, a second valve is arranged on the tubing between the reference cylinder and the pressure cylinder, and a third valve is arranged on the tubing between the reference cylinder and the sample cylinder.

Preferably, the venting and vacuumizing system comprises a venting tubing and a vacuum pump, the sample cylinder is respectively connected with the venting tubing and the vacuum pump through a tubing, a fourth valve is arranged on the venting tubing, and a fifth valve is arranged on the tubing of the vacuum pump.

Preferably, the temperature control system is a thermotank with a temperature adjusting function, and the reference cylinder, the pressure cylinder, the sample cylinder, the differential pressure sensor, the pressure gauge, the venting and vacuumizing system and the tubing and valve system are all placed in the thermotank.

Preferably, the sample cylinder is of a cylinder body structure with a cavity or is a core holder.

Based on the high-pressure helium shale porosity testing device, the present disclosure also provides a high-pressure helium shale porosity testing method, comprising the following steps:

firstly, preparation, installation and initialization of a sample:

crushing and screening a shale sample to 40-60 meshes, drying the sample according to experimental standards, and installing the sample into the sample cylinder; closing the first valve and the fourth valve, opening the second valve, the third valve and the fifth valve, and vacuumizing the whole system; after vacuumizing is completed, closing all the valves; and raising the temperature of the system to a target temperature;

secondly, saturation of the sample under a target pressure:

setting the helium pressure of a gas inlet to target pressure, opening the first valve, the second valve and the third valve, and waiting for the sample to be completely saturated by the helium; when the pressure is stable, recording the reading of the pressure gauge; closing the first valve and the third valve;

thirdly, a testing experiment:

setting helium pressure of the gas inlet to charge the reference cylinder and the pressure cylinder; when the pressure is stable, close the first valve; then, recording the reading of the differential pressure sensor and the reading of the pressure gauge respectively; after the second valve is closed, opening the third valve, and recording the reading of a differential pressure sensor; when the reading of the differential pressure sensor is unchanged, ending the experiment, and recording the reading of the differential pressure sensor at this time;

fourthly, calculation of porosity:

calculating the empty volume of the side of the sample cylinder through a formula; calculating the porosity of the sample through a formula;

fifthly, calculation of diffusing amount:

obtaining the relation between the dimensionless value of the diffusing amount and the time through a formula;

sixthly, repetition of the experiment:

in order to ensure the repeatability of the experiment, repeating the third step, the fourth step and the fifth step; and seventhly, an experiment of a next pressure point:

repeating the experiment at the beginning of the second step to test the porosity at another pressure point.

Compared with the prior art, the present disclosure has the following beneficial technical effects:

According to the high-pressure helium shale porosity testing device and method provided by the present disclosure, a pressure cylinder is used for reserving the pressure state of the reference cylinder before an experiment; the change of small pressure difference is directly measured by using a high-precision differential pressure sensor; real gas characteristics of helium under high pressure are considered during calculation, so that the testing precision of porosity under high pressure is comprehensively improved; the sample used in the experiment can be a core sample or a rock debris or powder sample; and the high-precision porosity test under the conditions of simulating stratum temperature and pressure under the high-pressure helium condition can be realized. Meanwhile, the relation between the diffusing amount of high-pressure helium in shale and the time can be obtained.

BRIEF DESCRIPTION OF THE DRAWINGS

To more clearly illustrate the embodiment of the present disclosure or the technical scheme in the prior art, the following briefly introduces the attached figures to be used in the embodiment. Apparently, the attached figures in the following description show merely some embodiments of the present disclosure, and those skilled in the art may still derive other drawings from these attached figures without creative efforts.

Reference signs: 1, reference cylinder; 2, pressure cylinder; 3, sample cylinder; 4, differential pressure sensor; 5, pressure gauge; 6, helium source; 7, first valve; 8, second valve; 9, third valve; 10, fourth valve; 11, fifth valve; 12, vacuum pump; 13, venting tubing; and thermotank.

DETAILED DESCRIPTION OF THE EMBODIMENTS

The following clearly and completely describes the technical scheme in the embodiments of the present disclosure with reference to the attached figures in the embodiments of the present disclosure. Apparently, the described embodiments are merely a part rather than all of the embodiments of the present disclosure. Based on the embodiment in the present disclosure, all other embodiments obtained by the ordinary technical staff in the art under the premise of without contributing creative labor belong to the scope protected by the present disclosure.

The present disclosure aims to provide a high-pressure helium shale porosity testing device and method so as to solve problems existing in the prior art.

To make the foregoing objective, features and advantages of the present disclosure clearer and more comprehensible, the present disclosure is further described in detail below with reference to the attached figures and specific embodiments.

Figure 1:
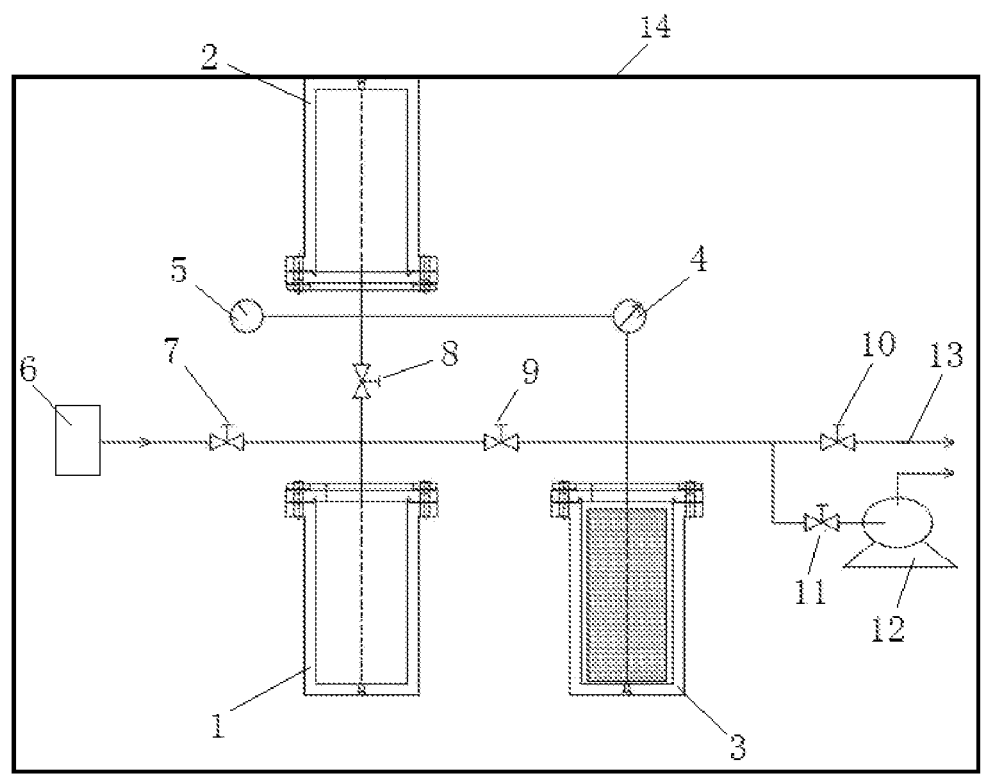
FIG. 1 is a structural schematic diagram of a high-pressure helium shale porosity testing device in the present disclosure.

The high-pressure helium shale porosity testing device in the embodiment, as shown in FIG. 1, comprises a reference cylinder 1, a pressure cylinder 2, a sample cylinder 3, a differential pressure sensor 4, a pressure gauge 5, an venting and vacuumizing system, a temperature control system and a tubing and valve system, wherein the reference cylinder 1 is respectively connected with a helium source 6, the pressure cylinder 2 and the sample cylinder 3 through the tubing and valve system, the differential pressure sensor 4 is arranged between the sample cylinder 3 and the pressure cylinder 2, the pressure gauge 5 is arranged at the pressure cylinder 2, the sample cylinder 3 is further connected with the venting and vacuumizing system through the tubing and valve system, and the temperature control system is used for controlling the temperature of the whole device.

In the specific embodiment, the tubing and valve system comprises tubings and valves, a first valve 7 is arranged on the tubing between the helium source and the reference cylinder 1, a second valve 8 is arranged on the tubing between the reference cylinder 1 and the pressure cylinder 2, and a third valve 9 is arranged on the tubing between the reference cylinder 1 and the sample cylinder 3; and the venting and vacuumizing system comprises an venting tubing 13 and a vacuum pump 12, the sample cylinder 3 is respectively connected with the venting tubing 13 and the vacuum pump 12 through tubings, a fourth valve 10 is arranged on the venting tubing 13, and a fifth valve 11 is arranged on the tubing of the vacuum pump 12.

In the specific embodiment, the temperature control system is a thermotank 14 with a temperature adjusting function, and the reference cylinder 1, the pressure cylinder 2, the sample cylinder 3, the differential pressure sensor 4, the pressure gauge 5, the venting and vacuumizing system and the pipe valve system are all placed in the thermotank 14.

In the specific embodiment, the sample cylinder 3 is of a cylinder body structure with a cavity or is a core holder.

The total volume of the reference cylinder 1 and connected tubing of the reference cylinder 1 needs to be precisely calibrated. The volume of the reference cylinder 1 is about half of the volume of the sample cylinder 3 to provide optimal accuracy. The pressure cylinder 2 is used for retaining and maintaining the pressure of the reference cylinder 1 before each step of the experiment. The volume of the pressure cylinder 2 coincides with that of the reference cylinder 1. The total volume of the sample cylinder 3 and connected tubings of the sample cylinder 3 needs to be precisely calibrated.

In the specific embodiment, the measurement accuracy of the pressure sensor is 0.1% of the full scale, for example, the maximum design air pressure of the system is 30 MPa, and the full scale of the pressure sensor is 30 MPa, namely the measurement accuracy of the pressure sensor is 30 KPa; the measurement accuracy of the differential pressure sensor 4 is also 0.1% of the full scale, for example, the tolerance pressure of the differential pressure sensor 4 is 30 MPa, but the full scale is plus and minus 250 KPa, and the measurement accuracy of the differential pressure sensor 4 can reach 0.5 KPa, which is much higher than that of a pressure sensor.

Based on the high-pressure helium shale porosity testing device, the embodiment also provides a high-pressure helium shale porosity testing method.

The system is filled with helium to a certain pressure $P_1$, after the pressure is not changed, the pressure of the reference cylinder 1 and the pressure of the pressure cylinder 2 are increased to $P_2$ at the same time, the connection between the pressure cylinder 2 and the reference cylinder 1 is cut off, and at the moment, the reading of the differential pressure sensor 4 is $\Delta P_0 = (P_2 - P_1)$. The helium enters the sample cylinder 3 from the reference cylinder 1, the reading $\Delta P$ of the differential pressure sensor 4 is recorded over time, and when the differential pressure is stable, the reading $\Delta P_f$ of the differential pressure sensor 4 is recorded. The compressibility factor of high-pressure helium needs to be considered during calculation. The mass conservation equation before and after measurement is firstly established:

$$\frac{P_1 V_2}{Z_1 RT} + \frac{P_2 V_r}{Z_2 RT} = \frac{P_3(V_r + V_2)}{Z_3 RT} \quad \text{(Formula I)}$$

Wherein, $V_r$ is the empty volume on the side of the reference cylinder 1; $V_2$ is the empty volume on the side of the sample cylinder 3 required to be measured; $P_3$ is the pressure of the sample cylinder 3 and the pressure of the reference cylinder 1 after the experiment, and is obtained through $P_2-\Delta P_f$ calculation instead of direct measurement; and $Z_1$, $Z_2$ and $Z_3$ are helium compression factors under the pressure of $P_1$, $P_2$ and $P_3$ and the temperature T respectively. Since the system is in a constant temperature state, R is the universal gas constant, and $\Delta P_0 = P_2 - P_1$, $\Delta P_1 = P_2 - P_3$, namely $P_1 = P_2 - \Delta P_0$, $P_3 = P_2 - \Delta P_f$, the formula I can be written as:

$$\frac{(P_2 - \Delta P_0)V_2}{Z_1} + \frac{P_2 V_r}{Z_2} = \frac{(P_2 - \Delta P)(V_r + V_2)}{Z_3} \quad \text{(Formula II)}$$

Thus it is obtained that the value of $V_2$ can be obtained through arrangement:

$$V_2 = \frac{P_2\left(\frac{1}{Z_2} - \frac{1}{Z_3}\right) + \frac{\Delta P}{Z_3}}{P_2\left(\frac{1}{Z_3} - \frac{1}{Z_1}\right) + \frac{\Delta P_0}{Z_1} - \frac{\Delta P}{Z_3}} V_r \quad \text{(Formula III)}$$

The precision of the pressure difference measured by the pressure difference sensor 4 is much higher than that of the pressure difference calculated by subtracting the pressure difference measured by the pressure difference sensor 4, so that the calculation precision of $V_2$ during measurement under high pressure is ensured.

Then, the volume occupied by the sample is as follows:

$$V_s = V_c - V_2 \quad \text{(Formula IV)}$$

Wherein, $V_s$ is the volume occupied by the sample; and $V_c$ is the initial volume on the side of the sample cylinder 3 without the sample.

The true density of the sample is as follows:

$$\rho_s = \frac{m}{V_s} \quad \text{(Formula V)}$$

Wherein, m is the total mass of the sample.

If the apparent density of the sample is known, the porosity of the sample is as follows:

$$\phi = 1 - \frac{\rho_b}{\rho_s} \quad \text{(Formula VI)}$$

wherein, $\rho_b$ is apparent density.

Meanwhile, the present disclosure also provides a method for measuring the diffusing amount of the high-pressure helium in the shale. During the above experiment, the amount of helium entering the shale sample at a certain moment is as follows:

$$\frac{P_1(V_c - V_b)}{Z_1 RT} + \frac{P_2 V_r}{Z_2 RT} - \frac{P(V_r + V_c - V_b)}{ZRT} \quad \text{(Formula VII)}$$

The maximum amount of helium finally entering the shale sample is as follows:

$$\frac{P_1(V_c - V_b)}{Z_1 RT} + \frac{P_2 V_r}{Z_2 RT} - \frac{P_3(V_r + V_c - V_b)}{Z_3 RT} \quad \text{(Formula VIII)}$$

The dimensionless diffusing amount entering into the shale sample is the ratio of the formula VII to the formula VIII, and can be measured directly by using the differential pressure sensor 4 and then arranged to be obtained as follows:

$$\frac{\frac{(P_2 - \Delta P_0)(V_c - V_b)}{Z_1} + \frac{P_2 V_r}{Z_2} - \frac{(P_2 - \Delta P)(V_r + V_c - V_b)}{Z}}{\frac{(P_2 - \Delta P_0)(V_c - V_b)}{Z_1} + \frac{P_2 V_r}{Z_2} - \frac{(P_2 - \Delta P_f)(V_r + V_c - V_b)}{Z_3}} \quad \text{(Formula IX)}$$

Figure 2:
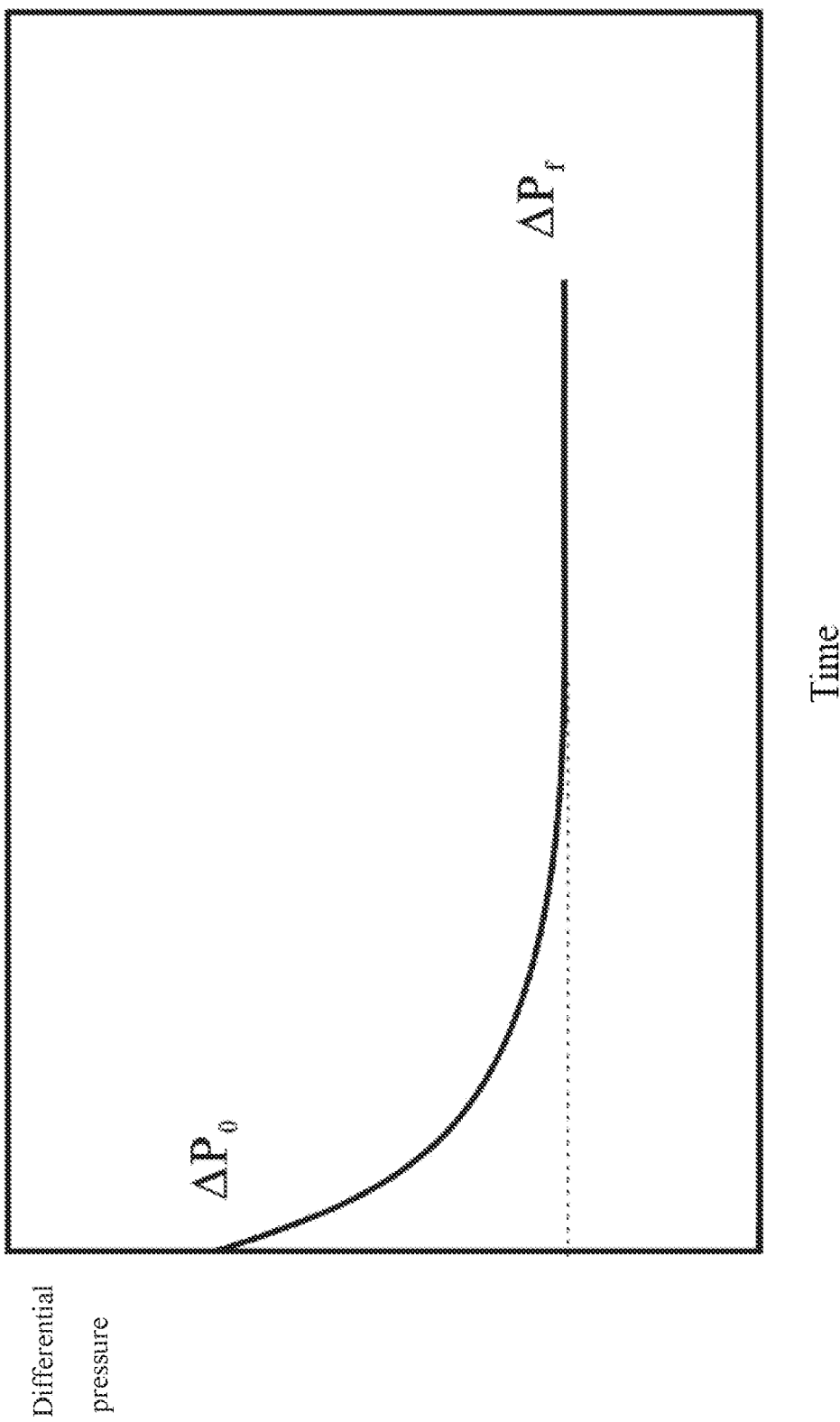
FIG. 2 is a schematic diagram of testing results of a differential pressure sensor before and after the experiment.
Figure 3:
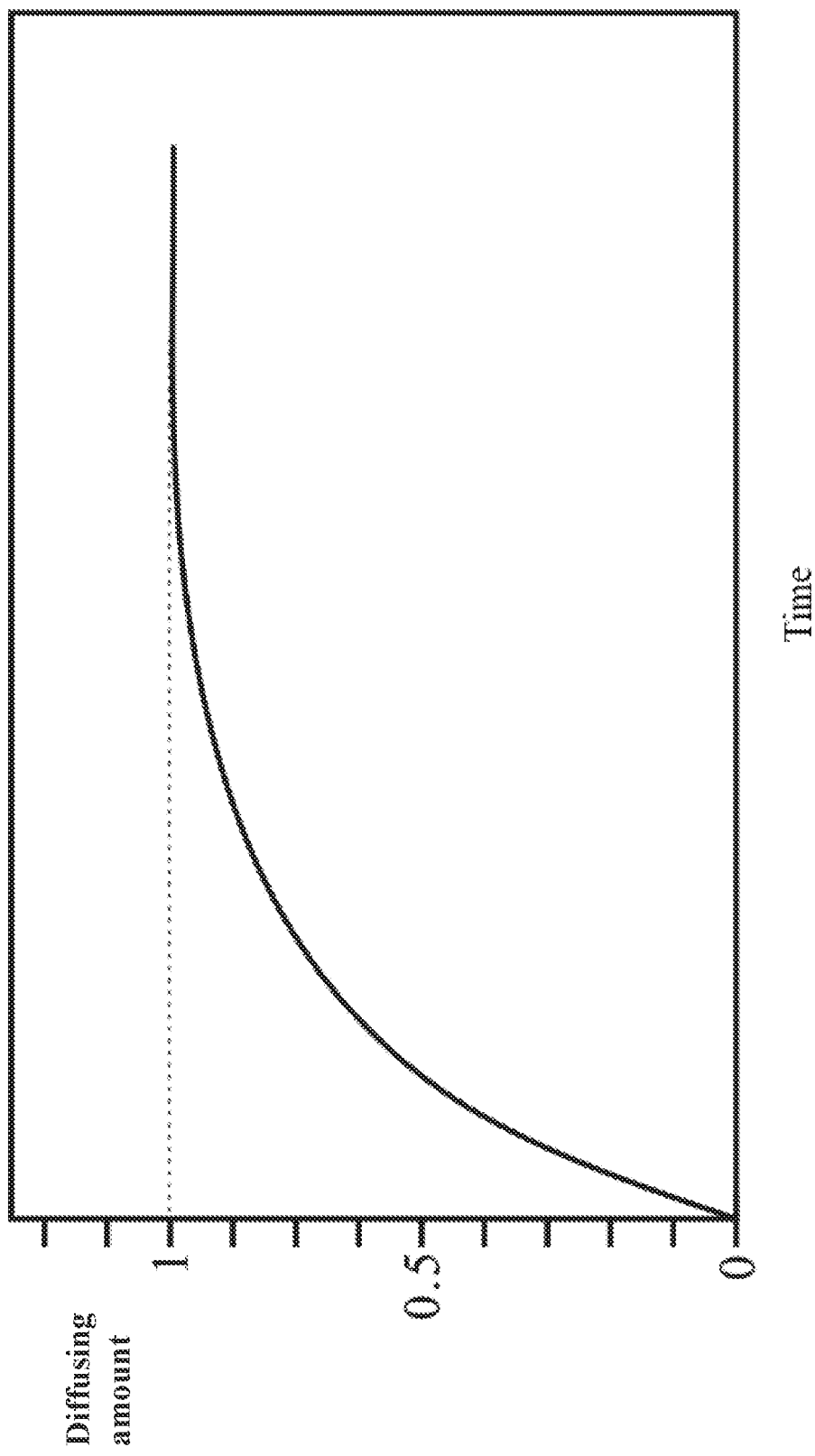
FIG. 3 is a schematic diagram of the relation between the diffusing amount after nondimensionalization and the time.

The testing method specifically comprises the following steps.

firstly, preparation, installation and initialization of a sample:

crushing and screening a shale sample to 40-60 meshes, drying the sample according to experimental standards, and installing the sample into the sample cylinder 3; closing the first valve 7 and the fourth valve 10, opening the second valve 8, the third valve 9 and the fifth valve 11, and vacuumizing the whole system; after vacuumizing is completed, closing all the valves; raising the temperature of the system to the target temperature;

secondly, saturation of the sample under a target pressure:

setting the helium pressure of a gas inlet to the target pressure, for example 10 MPa; opening the first valve 7, the second valve 8 and the third valve 9; waiting for the sample to be completely saturated by the helium; when the pressure is stable, recording the reading $P_1$ of a pressure gauge 5; closing the first valve 7 and the third valve 9;

thirdly, a testing experiment:

setting helium pressure of the gas inlet to about 10.2 MPa with the deviation of no more than 0.02 MPa; when the pressure is stable, recording the reading $\Delta P_0$ of the differential pressure sensor 4 and the reading $P_2$ of the pressure gauge 5 respectively;

opening the third valve 9 after the second valve 8 is closed, and automatically recording the reading $\Delta P$ (as shown in FIG. 2) of the differential pressure sensor 4;

when the $\Delta P$ is unchanged, ending the experiment, recording the $\Delta P$ at this time as $\Delta P_f$;

fourthly, calculation of porosity:

calculating the empty volume 2 of the side of the sample cylinder 3 through the formula 3; calculating the porosity of the sample through formulas 4, 5 and 6;

fifthly, calculation of diffusing amount:

obtaining the relation (as shown in FIG. 3) between the dimensionless value of the diffusing amount and the time through the formula 9;

sixthly, repetition of the experiment:

in order to ensure the repeatability of the experiment, repeating the third step, the fourth step and the fifth step; for example, calculating the porosity by repeating three to five times of the experiment with the helium pressure of 10 MPa; and seventhly, an experiment of a next pressure point:

repeating the experiment at the beginning of the second step, for example, increasing the overall pressure of the system to 20 MPa; performing the experiment and the calculation at the beginning of the third step so as to obtain the porosity of the sample under the pressure of 20 MPa.

The core sample can be used in the experiment, but the diffusion time of helium in the core sample is long, so that it needs to wait for longer time to achieve balance.

Examples are used for illustration of the principles and implementation methods of the present disclosure. The description of the embodiments is used to help illustrate the method and its core principles of the present disclosure. In addition, those skilled in the art can make various modifications in terms of specific embodiments and scope of application in accordance with the teachings of the present disclosure. In conclusion, the content of this specification shall not be construed as a limitation to the present disclosure.

What is claimed is:

1. A high-pressure helium shale porosity testing method of a high-pressure helium shale porosity testing device, the high-pressure helium shale porosity testing device comprising a reference cylinder, a pressure cylinder, a sample cylinder, a differential pressure sensor, a pressure gauge, a venting and vacuumizing system, a temperature control system and a tubing and valve system, wherein the reference cylinder is respectively connected with a helium source, the pressure cylinder and the sample cylinder through the tubing and valve system, the differential pressure sensor is configured to measure changes of pressure difference between the sample cylinder and the pressure cylinder, the pressure gauge is configured to measure pressure at the pressure cylinder, the sample cylinder is further connected with the venting and vacuumizing system through the tubing and valve system, and the temperature control system is used for controlling temperature of the high-pressure helium shale porosity testing device; wherein the method comprises the following steps:

firstly, preparation, installation and initialization of a sample:

crushing and screening a shale sample to 40-60 meshes, drying the sample according to experimental standards, and installing the sample into the sample cylinder; closing a first valve and a fourth valve, opening a second valve, a third valve and a fifth valve, and vacuumizing the whole system; after vacuumizing is completed, closing the first valve, the second valve, the third valve, the fourth valve and the fifth valve; raising the temperature of the system to a target temperature;

secondly, saturation of the sample under target pressure:

setting the helium pressure of a gas inlet to target pressure, opening the first valve, the second valve and the third valve, and waiting for the sample to be completely saturated by the helium; when the pressure is stable, recording the reading of the pressure gauge; closing the first valve and the third valve;

thirdly, a testing experiment:

setting helium pressure of the gas inlet; when the pressure is stable, recording the reading of the differential pressure sensor and the reading of the pressure gauge respectively; after the second valve is closed, opening the third valve, and recording the reading of the differential pressure sensor; when the reading of the differential pressure sensor is unchanged, ending the experiment, and recording the reading of the differential pressure sensor at this time;

fourthly, calculation of porosity:

calculating the empty volume of the side of the sample cylinder through a formula; calculating the porosity of the sample through formulas;

fifthly, calculation of diffusing amount:

obtaining the relation between the dimensionless value of the diffusing amount and the time through a formula;

sixthly, repetition of the experiment:

in order to ensure the repeatability of the experiment, repeating the third step, the fourth step and the fifth step; and seventhly, an experiment of a next pressure point:

repeating the experiment at the beginning of the second step to test the porosity at another pressure point.

2. The high-pressure helium shale porosity testing method according to claim 1, wherein the tubing and valve system comprises tubings and valves, the first valve is arranged on the tubing between the helium source and the reference cylinder, the second valve is arranged on the tubing between the reference cylinder and the pressure cylinder, and the third valve is arranged on the tubing between the reference cylinder and the sample cylinder.

3. The high-pressure helium shale porosity testing method according to claim 1, wherein the venting and vacuumizing system comprises a venting tubing and a vacuum pump, the sample cylinder is respectively connected with the venting tubing and the vacuum pump through tubings, a fourth valve is arranged on the venting tubing, and a fifth valve is arranged on the tubing of the vacuum pump.

4. The high-pressure helium shale porosity testing method according to claim 1, wherein the temperature control system is a thermotank with a temperature adjusting function, and the reference cylinder, the pressure cylinder, the sample cylinder, the differential pressure sensor, the pressure gauge, the venting and vacuumizing system and the tubing and valve system are all placed in the thermotank.

5. The high-pressure helium shale porosity testing method according to claim 1, wherein the sample cylinder is of a cylinder body structure with a cavity or is a core holder.

\* \* \* \* \*